United States Patent [19]

Renger

[11] Patent Number: 5,593,430
[45] Date of Patent: Jan. 14, 1997

[54] BUS SYSTEM FOR INTERCONNECTING AN IMPLANTABLE MEDICAL DEVICE WITH A PLURALITY OF SENSORS

[75] Inventor: Herman L. Renger, Calabasas, Calif.

[73] Assignee: Pacesetter, Inc., Sylmar, Calif.

[21] Appl. No.: 379,827

[22] Filed: Jan. 27, 1995

[51] Int. Cl.$^6$ ................................ A61N 1/365
[52] U.S. Cl. ................ 607/18; 607/19; 607/32; 607/60
[58] Field of Search ................ 607/9, 16–24, 607/2, 60, 32, 45, 6, 3, 120; 623/25

[56] References Cited

U.S. PATENT DOCUMENTS

| | | | |
|---|---|---|---|
| 4,399,820 | 8/1983 | Wirtzfeld et al. | 607/27 |
| 4,628,934 | 12/1986 | Pohndorf et al. | 607/9 |
| 4,877,032 | 10/1989 | Heinze et al. | 128/695 |
| 5,411,532 | 5/1995 | Mortazavi | 607/21 |

OTHER PUBLICATIONS

Borky et al., "Integrated Signal Conditioning or Silicon Pressure Sensors," IEEE Transactions on Electron Devices, vol. ED–26, No. 12, pp. 1906–1910 Dec. 1979.

*Primary Examiner*—Marvin M. Lateef
*Assistant Examiner*—Kennedy J. Schaetzle
*Attorney, Agent, or Firm*—Harold C. Schloss

[57] ABSTRACT

A two-conductor bus system is provided to electrically interconnect a plurality of physiologic sensors to a pacemaker, each sensor being adapted for placement along a pacing lead. The conductors of the bus extend longitudinally through the insulating material of the lead, connecting to each sensor. The pacemaker provides a supply voltage on the bus to provide power to the sensors. The sensors modulate the supply voltage on the bus to transmit information to the pacemaker. This information may be used by the pacemaker to adaptively pace the heart. In one embodiment, the sensors include bus monitoring circuitry for receiving control signals from the pacemaker.

12 Claims, 5 Drawing Sheets

BUS SYSTEM FOR INTERCONNECTING AN IMPLANTABLE MEDICAL DEVICE WITH A PLURALITY OF SENSORS

FIELD OF THE INVENTION

This invention relates to implantable sensors used to provide physiologic information to a pacemaker or other implantable medical device. In particular, this invention relates to a system and method for permitting a pacemaker or other implantable medical device to communicate with multiple implantable sensors.

BACKGROUND OF THE INVENTION

In a normally functioning heart, the sino-atrial (S-A) node generates electrical signals that control the contractions of the heart. These signals are generally in the form of quasi-periodic voltage impulses that are of sufficient magnitude to cause the contraction of the heart muscle. In a single cycle of the heart, a signal (i.e., a voltage impulse) is generated by the S-A node, causing the right and left atria to contract. The contractions of the right and left atria force blood into the corresponding right and left ventricles. The signal is also conducted through the AV node to the right and left ventricles (after a short time delay), causing the right and left ventricles to contract.

Various disorders in the cardiac electro-physiological system can cause abnormalities in the rate and/or the timing of the contractions of the heart. For example, a malfunctioning AV node conduction system can delay or prevent the transmission of the signal to the right and left ventricles, impairing or preventing the stimulation of the ventricles. Such disorders can often be corrected by use of a cardiac pacemaker.

Cardiac pacing involves the electrical stimulation of the heart in order to control the timing of the contractions of the heart. Electrical stimuli in the form of pulses are generated by a battery-powered pacemaker and applied to the tissue of the heart by one or more electrodes that are connected to the pacemaker via flexible, insulated conductors. The electrical stimuli supplement or supersede the electrical signals generated by the S-A node. The insulated conductors and associated electrodes form what is referred to as the "pacing lead." In addition to being used to apply pulses to the heart, the electrode (or electrodes) of a pacing lead may be used to sense intrinsic electrical activity within the heart.

Modern pacemakers commonly use a pacing technique known as "atrial tracking," wherein intrinsic electrical activity sensed within the right atrium is used to control the timing of pulses applied to the right ventricle. A pacemaker may be programmed, for example, so that each time an intrinsic electrical impulse is sensed in the right atrium, the pacemaker waits for a preprogrammed time delay (e.g., 75 milliseconds) and then applies a pulse to the right ventricle. Atrial tracking ensures that the ventricles contract shortly after each atrial contraction, and thus ensures that the atria and ventricles contract at the same rate.

Atrial tracking generally works well provided that the S-A node responds to the metabolic demand of the body by appropriately adjusting the rate at which impulses are applied to the atria. In certain situations, however, the intrinsic signal activity in the right atrium serves as a poor rate-setting mechanism for pacing the ventricles. Such situations include sinus bradycardia, fixed atrial fibrillation, giant silent atrium, and the bradycardia-tachycardia syndrome. Since disorders of this type are fairly common, it has recently become common to use an implantable physiologic sensor to provide information to the pacemaker that allows the pacemaker to estimate metabolic demand and adjust the pacing rate accordingly. This form of pacing is commonly known as "rate adaptive" or "rate responsive" pacing. Information provided by the physiologic sensor may also be used by the pacemaker to determine how the heart is responding to a particular pacing pattern. Further, information provided by the sensor may be conveyed to a doctor (using conventional telemetry techniques) to facilitate detection of abnormalities in the operation of the heart.

Various types of implantable sensors can be used to provide information to the pacemaker. One common type of sensor, for example, is a motion sensor that uses a piezoelectric device to sense low frequency motion associated with muscular activity. The output of the motion sensor is typically in the form of an analog signal, the amplitude and frequency of which indicate the degree of motion. When a high degree of motion is indicated by the signal, indicating increased physical activity, the pacemaker increases the rate at which pulses are applied to the right ventricle to increase the output of the heart. Other types of physiologic sensors that may be used by the pacemaker include, for example, blood pressure sensors, oxygen saturation sensors, respiratory-rate sensors, flexure sensors, flow sensors, carbon dioxide sensors, and temperature sensors.

It is known in the art to mount a physiologic sensor along a pacing lead in order to facilitate implantation of the sensor. The information signal generated by the lead-mounted sensor is conveyed to the pacemaker along a pair of conductors that are embedded within the insulating material of the pacing lead and which extend longitudinally through the lead. Each conductor is terminated at the proximal end of the lead with a connector pin that is adapted for insertion into a corresponding feed-through connector on the housing of the pacemaker, allowing electrical connection to be established between the sensor and the pacemaker once the lead has been inserted into the heart.

Existing physiologic sensors that are adapted for placement along the pacing lead are designed to communicate over dedicated pairs of signal conductors. Thus, in order to provide multiple sensors along a pacing lead, it is necessary to pass multiple pairs of signal conductors within the pacing lead—one pair of signal conductors per sensor. It is also necessary to provide a dedicated pair of connector pins and a dedicated pair of feed-though connectors for each sensor, and to provide a separate receiver circuit within the pacemaker for each sensor. These additional hardware requirements increase the cost and complexity of the pacing apparatus and the complexity of the implantation procedure, and have accordingly deterred pacemaker manufacturers from providing multiple sensors along a lead.

A need thus exists in the art for a system that allows sensors to be added to the pacing system without a corresponding increase in the number of conductors that must be passed through the pacing lead and connected to the pacemaker.

SUMMARY OF THE INVENTION

In accordance with the present invention, a two-conductor bus system is provided for interconnecting a plurality of physiologic sensors to a pacemaker. The two conductors of the bus are formed as helical coils that extend longitudinally through at least a portion of the pacing lead. Each sensor is mounted on the lead and connected to the bus. The pacemaker provides a supply voltage on the bus. Each sensor receives current from the pacemaker over the bus, and uses at least a portion of the current to provide power to active components of the sensor. Each sensor modulates the supply voltage on the bus to transmit an information signal to the pacemaker. The pacemaker uses the information obtained from the multiple sensors to adaptively pace the heart and/or sense abnormalities in the operation of the heart.

In an analog embodiment of the invention, a motion sensor is provided that transmits a motion signal to the pacemaker as a pulse-rate modulated signal within a predetermined frequency range. The pulse-rate modulated signal is generated using the output of a piezoelectric accelerometer to control the frequency at which the motion sensor accepts pulses of current from the bus. The pacemaker uses a comparator to detect the voltage pulses on the bus, and uses a phase-locked loop to separate the signal of the motion sensor from pulse-rate modulated signals generated by other sensors.

In a digital embodiment of the invention, a microprocessor-controlled pressure sensor is provided that is capable of both sending data to the pacemaker and receiving control signals (e.g., addresses and commands) from the pacemaker. Information is transferred between the pacemaker and pressure sensor (and other sensors on the bus) by generating positive pulses on the bus in accordance with a predetermined modulation technique. To generate a single pulse on the bus, the pressure sensor uses a first switching transistor to charge a capacitor from the bus, and then uses a second switching transistor to apply the capacitor voltage to the bus. The pacemaker uses a similar dual-transistor configuration to transmit pulses to sensors. The pressure sensor and pacemaker each include a bus monitoring circuit that includes a coupling capacitor and a comparator. Other sensors connected to the bus include similar or identical pulse generation and bus monitoring circuitry to that of the pressure sensor. In accordance with a preferred method of operation, the pacemaker transmits an address signal on the bus to select a single sensor, and the addressed sensor responds by transmitting its data to the pacemaker.

The present invention reduces the cost and complexity associated with providing multiple sensors along a pacing lead by eliminating the need to pass dedicated pairs of conductors between the pacemaker and each sensor. The reduction in the number of conductors required produces a corresponding reduction in the number of connector pins on the lead on and feed-through connectors on the pacemaker housing. Other features and advantages of the present invention will be apparent from the detailed description which follows.

DETAILED DESCRIPTION OF THE PREFERRED EMBODIMENTS

The present invention comprises a two-conductor bus system for connecting multiple sensors to an implantable medical device such as a pacemaker. The bus system of the present invention is described herein in the context of pacemakers. As will be apparent to those skilled in the art, however, the bus system may be used with other types of implantable medical devices, including neural stimulators used with prosthetic devices, defibrillators, and drug pumps.

Figure 1:
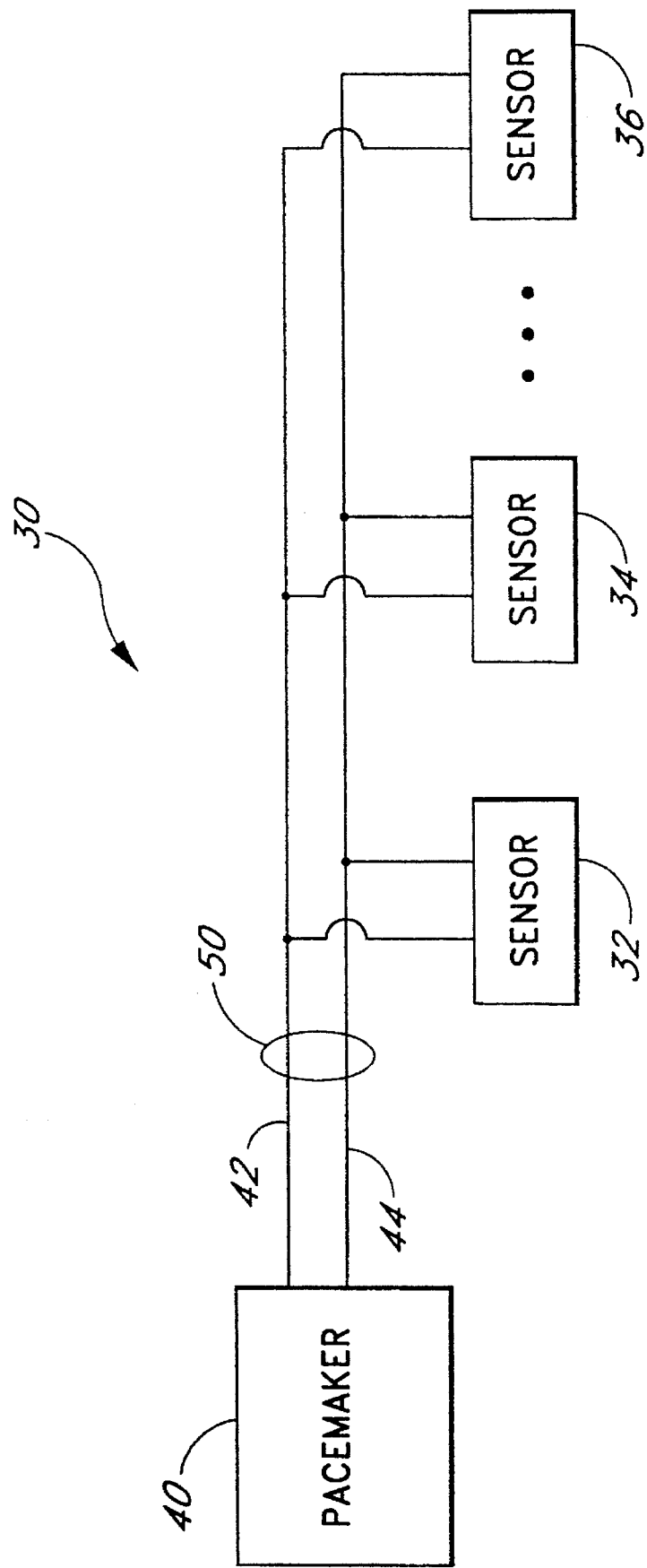
FIG. 1 is schematic diagram illustrating a plurality of physiologic sensors connected to a pacemaker by a two-conductor bus in accordance with the present invention.

FIG. 1 illustrates a bus system 30 in accordance with the present invention. The bus system 30 comprises a plurality of physiologic sensors 32, 34, 36. Illustratively, the sensors 32, 34 and 36 may be a temperature sensor, an oxygen saturation sensor, and a pressure sensor, respectively. The sensors are connected to a pacemaker 40 by conductors 42 and 44. The conductors 42 and 44 form a two-conductor bus 50. Additional sensors (not shown) may be connected to the two-conductor bus 50, as represented by the ellipsis in FIG. 1.

Figure 2:
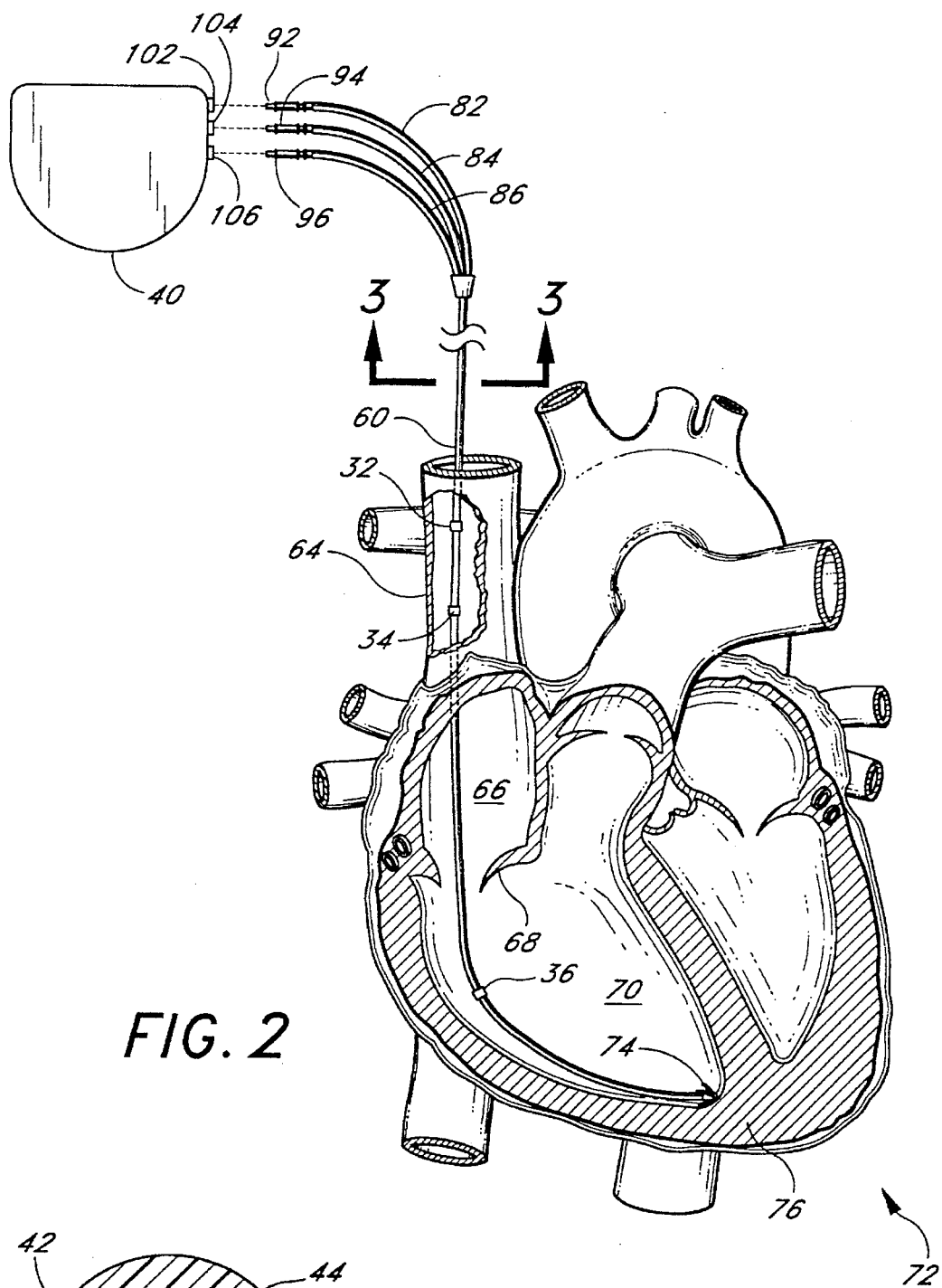
FIG. 2 is a perspective view in partial cross section showing the sensors of FIG. 1 mounted along a pacing lead that is implanted within a human heart, and showing a pacemaker to which the pacing lead connects.

Each sensor 32, 34, 36 is configured for placement along a pacing lead (as shown in FIG. 2), and is designed to communicate with the pacemaker 40 over the bus 50 without interfering with the operation of the other sensors. This manner of interconnecting sensors to a pacemaker reduces the number of conductors that must be passed through the lead, and thereby facilitates the placement of multiple sensors along the pacing lead. To eliminate the need for separate power sources, each sensor 32, 34, 36 is designed to receive power from the pacemaker 40 over the bus 50.

The sensors 32, 34, 36 generate physiologic data that corresponds to the metabolic demand of the body and/or the performance of the heart. The pacemaker 40 uses this information to adjust various pacing parameters such as the ventricular pacing rate. The pacemaker 40 may also use this information to detect various abnormalities in the operation of the heart. Information received from the sensors 32, 34, 36 or derived from sensor data may be communicated from the pacemaker 40 to a physician using conventional telemetry techniques.

The two-conductor bus 50 serves the dual purpose of supplying power from the pacemaker 40 to each of the sensors 32, 34, 36, and conveying information between the pacemaker 40 and each sensor 32, 34, 36. Communication between the pacemaker 40 and a given sensor 32, 34, or 36 may be either unidirectional or bi-directional, depending upon the design of the particular sensor. Communication will be unidirectional if the sensor is designed to send information to the pacemaker 40 only, and is not designed to receive information from the pacemaker 40. Communication may be bi-directional if the sensor is designed to send information to the pacemaker 40 and to receive commands or other control information from the pacemaker 40.

In operation, the pacemaker 40 supplies power to the sensors 32, 34, 36 by providing a DC supply voltage on the bus 50. The pacemaker 40 may supply the voltage continuously, or may alternatively supply the voltage only when information samples are to be taken from one or more of the sensors 32, 34, 36. Each sensor 32, 34, 36 accepts current from the pacemaker 40 over the bus 50. At least a portion of this current is used to supply power to the circuitry of the respective sensor 32, 34, 36.

To communicate data to the pacemaker 40, each sensor 32, 34, 36 modulates the supply voltage and/or current on the bus 50 in accordance with a predetermined modulation technique. This may be done, for example, by accepting current from the bus 50 in a controlled manner to generate voltage and/or current pulses on the bus 50. The pacemaker 40 monitors the voltage on the bus 50 (or equivalently, monitors the current on the bus 50) to receive information from the sensors 32, 34 and 36. The pacemaker 40 may additionally modulate the supply voltage to transfer information to one or more of the sensors 32, 34, 36. Any suitable modulation or encoding technique may be used for transferring information between the pacemaker 40 and the sensors 32, 34, 36, such as pulse-width modulation or pulse rate modulation. Further, any suitable signal-separation technique may be used to permit differentiation between information signals generated by or provided to different sensors, including frequency division multiplexing, time division multiplexing, and sensor addressing.

FIG. 2 illustrates how the sensors 32, 34 and 36 may be positioned along a pacing lead 60. The lead 60 is shown in FIG. 2 extending through the superior vena cava 64, right atrium 66, tricuspid valve 68 and right ventricle 70 of a human heart 72, with a ventricular electrode 74 of the lead 60 positioned in the right ventricular apex 76. The lead 60 separates into three separate branches 82, 84 and 86 at its proximal end. The branches 82, 84 and 86 are terminated with respective connector pins 92, 94 and 96 that are configured to plug into corresponding feed-through connectors 102, 104 and 106 on the housing of the pacemaker 40. Two of the three connector pins are conductively connected to respective conductors 42 and 44 (FIG. 1) of the bus 50. The third connector pin is conductively connected to the ventricular electrode 74.

The sensors 32, 34 and 36 are shown in FIG. 2 mounted along the body of the lead 60 such that the sensors 32 and 34 are positioned within the superior vena cava 64, and the sensor 36 is positioned within the right ventricle 70. As will be recognized by those skilled in the art, the respective positions at which the sensors are mounted along the lead 60 depend upon the types of sensors used and the purposes for which they are provided. For example, it may be desirable to place a pressure sensor within the right ventricle 70 to measure changes in pressure during ventricular contractions, or to place a flexure sensor in the region of the tricuspid valve 68 to measure the degree of flexure of the lead 60 during atrial and ventricular contractions. It may further be desirable to place one or more of a temperature sensor, a flow sensor, an oxygen saturation sensor and a motion sensor in the superior vena cava 64. It may also be desirable to place or more sensors of the same type along the lead 60 to provide redundancy. While the sensors 32, 34 and 36 are shown in FIG. 2 as being mounted along a unipolar (i.e., single electrode), ventricular pacing lead, it should be understood that the present invention also applies to other types of leads, including atrial leads, ventricular leads and single-pass A-V leads of both unipolar or bipolar types.

Figure 3:
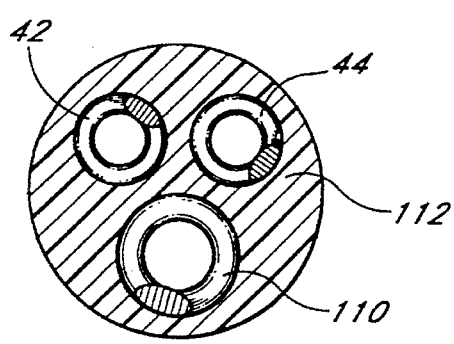
FIG. 3 is a cross sectional view taken along the line 3—3 of FIG. 2, showing the conductors of the two-conductor bus of FIG. 1.

Referring to FIG. 3, the lead 60 comprises three conductors 42, 44, and 110 that are formed within an insulating material 112 such as silicone rubber, and which extend longitudinally from the proximal end of the lead 60. The conductors 42 and 44 are the conductors of the bus 50 shown in FIG. 1. To provide a high degree of durability, the conductors 42 and 44 are formed as helical coils, as is conventional for conductors used to transmit pacing signals (such as the conductor 110, which is similarly formed as a helical coil). However, non-helical-coil type conductors could be used. Referring to FIGS. 2 and 3, the conductor 110 is connected to the ventricular electrode 74 at one end and to the pin connector 92 at the opposite end. The helical coil of the conductor 110 is formed with a slightly larger diameter than the helical coils of the conductors 42 and 44 to facilitate insertion of a stylet (i.e., guidewire) during an implantation procedure. The conductors 42 and 44 are connected to the pin connectors 94 and 96 respectively, and are connected to each of the sensors 32, 34 and 36, as shown in FIG. 1. Although the conductors 42, 44 and 110 are shown in FIG. 3 as extending side-by-side one another, other types of arrangements are possible. For example, the conductors 42, 44 and 110 could be arranged coaxially (i.e., one inside the other), with the conductor 110 as the inner-most conductor. Alternatively, all three conductors 42, 44 and 110 could be formed within a single, multi-filar helical coil.

As noted above, physiologic sensors used for pacing applications have heretofore been designed to communicate with the pacemaker over dedicated sets of conductors, making it difficult and expensive to place multiple sensors along a pacing lead. The present invention solves this problem by providing pacemaker and sensor circuitry that allows multiple sensors to communicate with the pacemaker over a single conductor pair. The present invention thereby reduces the number of electrical connections required between the sensors and the pacemaker to two (as shown in FIG. 1), regardless of the number of sensors provided along the lead 60. Since only two conductors are used to electrically interconnect the pacemaker 40 to the sensors 32, 34, 36, only two pin connectors 94, 96 and two feed-through connectors 104, 106 are needed for sensor operation. The present invention thus significantly reduces the cost and complexity of providing multiple sensors along a pacing lead.

Figure 4:
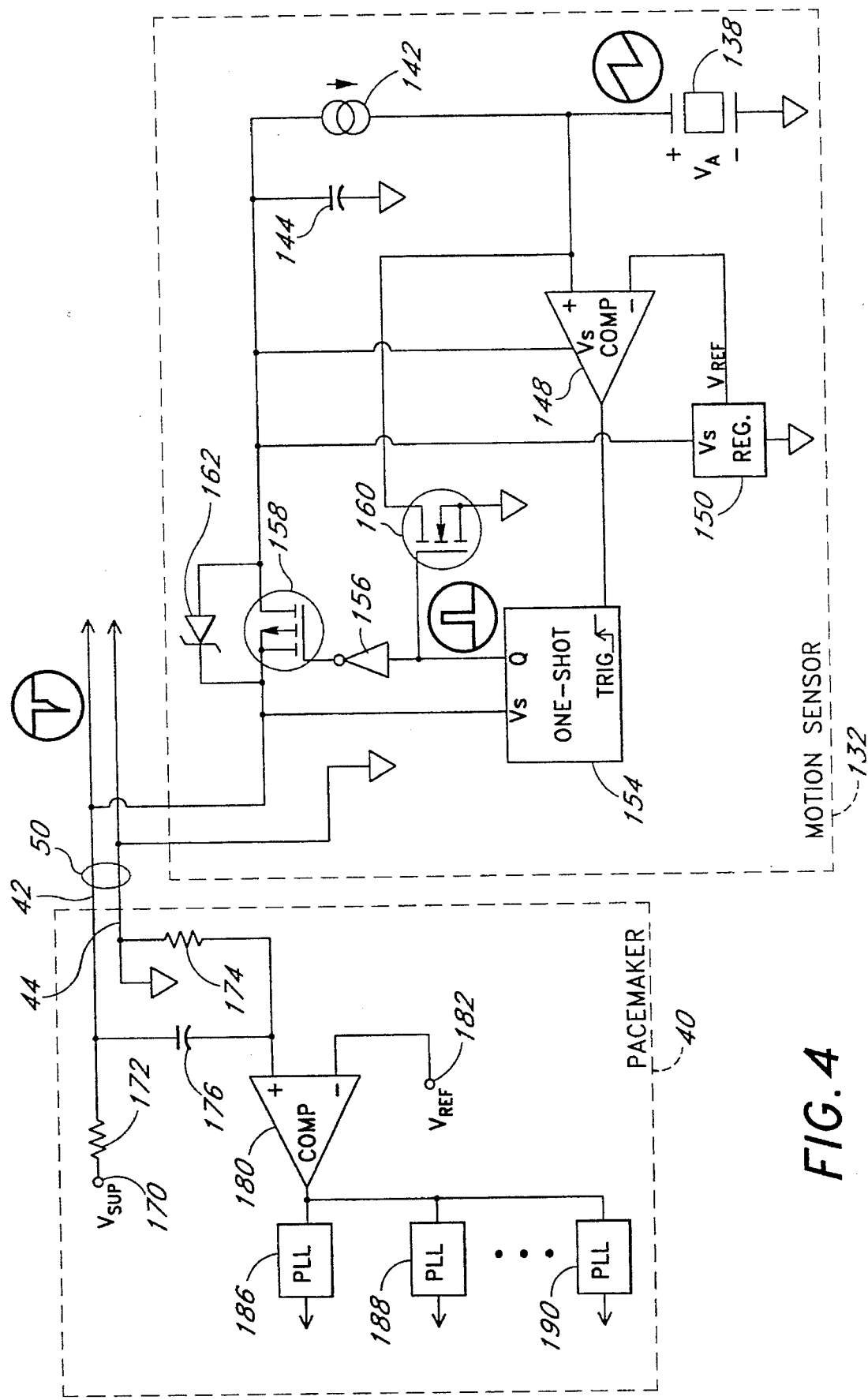
FIG. 4 is a circuit diagram for a motion sensor in accordance with the present invention, and for a pacemaker circuit that provides power to and receives signals from multiple sensors over a two-conductor bus. Waveforms shown in FIG. 4 illustrate the general form of voltage signals that occur at indicated nodes of the circuit (relative to local ground) during a motion sensing cycle.

Various embodiments of pacemaker and sensor circuitry will now be described. FIG. 4 illustrates the circuitry of a motion sensor 132 and a pacemaker 40 in accordance with an analog embodiment of the present invention. The motion sensor 132 and pacemaker 40 are connected by the two conductor bus 50, which comprises the lines 42 and 44. The motion sensor 132 conveys a motion (i.e., acceleration) signal to the pacemaker 40 over the bus 50 as a pulse-rate modulated signal. The motion sensor 132 and pacemaker 40 are designed such that multiple sensors can transmit signals to the pacemaker 40 over the bus 50 simultaneously. A motion sensor of the type shown can be used for various pacing-related purposes. For example, the motion sensor 132 could be positioned within the heart and used to detect abnormal contraction patterns (e.g., fibrillation), or could be positioned closer to the proximal end of the lead 60 and used to detect levels of physical activity of the patient. Referring to the pacemaker 40 in FIG. 4, only the circuitry for providing sensor power and for receiving sensor signals over the bus 50 is shown.

The motion sensor 132 comprises a piezoelectric accelerometer 138, a constant current source 142, a capacitor 144, a comparator (COMP) 148, a voltage regulator 150, a one-shot 154, an inverter 156, two switching transistors 158 and 160 (shown as a P-channel enhancement mode MOS- FET and an N-channel enhancement mode MOSFET respectively, each having the source connected to the body), and a zener diode 162. One terminal of the accelerometer 138 is connected to local ground. The other terminal of the accelerometer 138 is connected to the output side of the constant current source 142, to the positive input of the comparator 148, and to the drain of the transistor 160. One end of the capacitor 144 is connected to local ground. The other end of the capacitor 144 is connected to the input side of the constant current source 142, to the supply input ($V_S$) of the comparator 148, to the supply input ($V_S$) of the voltage regulator 150, to the drain of the transistor 158, and to the anode of the diode 162. The output of the comparator 148 is connected to the trigger (TRIG) input of the one-shot 154. The output of the voltage regulator 150 is connected to the negative input of the comparator 148. The output (Q) of the one-shot 154 is connected to the inverter 156, and to the gate of the transistor 160. The output of the inverter 156 is connected to the gate of the transistor 158. The supply input ($V_S$) of the one-shot 154, the source of the transistor 158, and the cathode of the diode 162 are connected to the bus line 42.

The circuitry of the pacemaker 40 includes a supply voltage source 170 that generates a DC voltage $V_{SUP}$ (typically 3 to 5 volts), a first resistor 172, a second resistor 174, a coupling capacitor 176, a comparator 180, a reference voltage source 182 that generates a negative DC reference voltage $V_{REF}$ (typically −0.1 volts), and a plurality of phase-locked loops (PLLs) 186, 188 and 190 (one phase-locked loop per sensor). One end of the resistor 172 is connected to the supply voltage source 170. The other end of the resistor 172 is connected to the bus line 42, and to one terminal of the capacitor 176. The other terminal of the capacitor 176 is connected to the positive input of the comparator 180, and to one end of the resistor 174. The other end of the resistor 174 is connected to the bus line 44. The negative input of the comparator 180 is connected to the reference voltage source 182. The output of the comparator 180 is connected the respective signal inputs of the phase-locked loops 186, 188 and 190.

The operation of the pacemaker and sensor circuits of FIG. 4 will now be described. The supply voltage source 170 of the pacemaker 40 generates a DC supply voltage $V_{SUP}$ (typically 3 to 5 volts), producing a voltage of approximately $V_{SUP}$ between the bus lines 42 and 44. The supply voltage $V_{SUP}$ may be supplied continuously, or may be turned on periodically to take samples from the motion sensor 132 (and other sensors on the bus 50). When the supply voltage $V_{SUP}$ is switched on, a small amount of current flows through the diode 162, causing the capacitor 144 to become charged. The charge stored by the capacitor is used to power the constant current source 142, comparator 148, voltage regulator 150, and one-shot 154 of the motion sensor 132.

Once the capacitor 144 becomes charged, the constant current source 142 provides an approximately constant current to the accelerometer 138, causing the voltage $V_A$ across the accelerometer 138 to increase as the accelerometer 138 becomes charged. If the motion sensor 132 (and thus the accelerometer 138) is not accelerating, the voltage $V_A$ increases at its average rate. This average rate is determined by the parameters of the accelerometer 138 and the magnitude of the current produced by the constant current source 142. If the motion sensor 132 is accelerating (as the result, for example, of muscular activity by the patient), the accelerometer 138 internally generates a charge that is added to the charge attributable to the constant current source 142, causing the voltage $V_A$ to increase at a different rate. The charge generated internally by the accelerometer 138 is proportional to acceleration. Thus, the voltage $V_A$ increases at a rate that is proportional to the degree of acceleration of the motion sensor 132.

The voltage regulator 150 outputs an approximately constant DC reference voltage $V_{REF}$, which is provided at the negative input of the comparator 148. When the voltage $V_A$ is less than $V_{REF}$, the comparator 148 outputs a logic low voltage level. With the output of the comparator 148 at a logic low level, the output (Q) of the one-shot 154 remains low, maintaining the transistors 158 and 160 in an non-conductive or "off" state. When the voltage $V_A$ exceeds $V_{REF}$, the output of the comparator 148 switches to a logic high voltage level. This low-to-high transition at the output of the comparator 148 causes the one shot 154 to fire, producing a short voltage pulse of a fixed duration at the output (Q) of the one shot 154. This pulse causes the transistor 158 to turn on for the duration of the pulse, allowing the capacitor 144 to recharge as the motion sensor 132 accepts a pulse of current from the bus 50. The one shot 154 is selected such that the duration of the one-shot output pulse is long enough to allow the capacitor 144 to become sufficiently charged. As the motion sensor 132 accepts a pulse of current, the voltage on the bus 50 drops below $V_{SUP}$ (typically by a few tenths of a volt) as the result of current flowing through the resistor 172. Thus, a negative pulse (i.e., a temporary decrease in voltage) is generated on the bus 50.

The pulse at the output of the one-shot 154 also causes the transistor 160 to turn on for the duration of the pulse, temporarily shorting the accelerometer 138 to local ground. This causes the accelerometer 138 to discharge (through the transistor 160), returning the voltage $V_A$ to approximately zero. A new motion-sensing cycle then begins, and with $V_A$ increasing until it exceeds $V_{REF}$, at which time the next pulse of current is accepted. Since the rate at which $V_A$ increases is proportional to the degree of acceleration of the motion sensor 132, the distance between consecutive pulses is inversely related to the acceleration.

Figure 5:
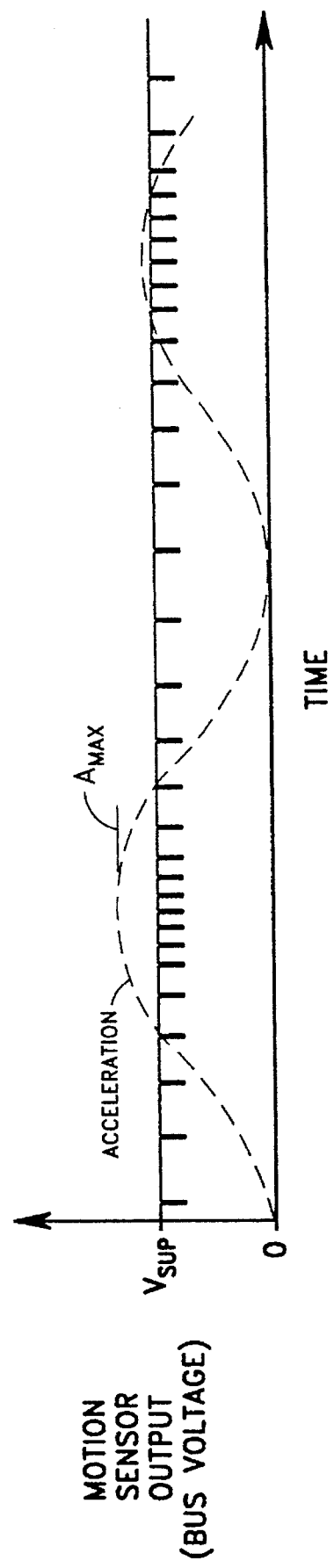
FIG. 5 is a timing diagram for the circuit of FIG. 4, illustrating a pulse-rate modulated signal generated by the motion sensor in response to a varying level of acceleration.

FIG. 5 shows the general form of the motion sensor output signal (i.e., the voltage on the bus 50 assuming no other sensors are transmitting) for varying levels of acceleration. When acceleration is zero, the motion sensor 132 generates pulses at its minimum rate. This minimum pulse rate is determined by the parameters of the constant current source 142, the accelerometer 138, and the voltage regulator 150. As acceleration becomes non-zero, the pulse frequency increases in proportion to the level of acceleration. A maximum pulse frequency is approached as acceleration approaches $A_{MAX}$, which is the maximum acceleration for which the accelerometer 138 is designed. Thus, the pulse frequency varies within a fixed (and predetermined) range as acceleration varies.

Referring again to FIG. 4, the pacemaker 40 detects the negative pulses on the bus 50 using a bus monitoring circuit that comprises the coupling capacitor 176, comparator 180, and reference voltage source 182. When no pulses appear on the bus 50, the coupling capacitor 176 filters out the DC bus voltage, producing a voltage of approximately zero at the positive input of the comparator 180. Since the negative input of the comparator 180 is maintained at a negative reference voltage $V_{REF}$, the comparator 180 outputs a logic high value. When a negative pulse appears on the bus 50, the voltage at the positive input of the comparator 180 briefly drops below the negative reference voltage $V_{REF}$, causing the comparator to switch to a logic low level. The pulse signal on the bus 50 is thus reproduced at the output of the comparator 180 in an amplified form.

The output of the comparator 180 is fed to the signal inputs of the phase-locked loops 186, 188, 190. Each phase-locked loop detects a pulse signal within a predetermined frequency range corresponding to the pulse frequency range of a specific sensor. Thus for example, the phase-locked loops 186, 188 and 190 may be designed to detect the pulse signals of 900 to 1100 pulses per second, 1800 to 2200 pulses per second, and 2700 to 3300 pulses per second respectively, corresponding to the output frequencies of three different sensors. As will be recognized by those skilled in the art, the phase-locked loops 186, 188 and 190 could be replaced by a CPU or DSP chip programmed to isolate the sensor signals using conventional filtering techniques. The signal at the output of the phase-locked loop which corresponds to the motion sensor 132 is the demodulated acceleration signal. This signal may be digitized and periodically sampled by the central processing unit (not shown) of the pacemaker 40, and used to adjust the rate of ventricular stimulation.

Figure 6:
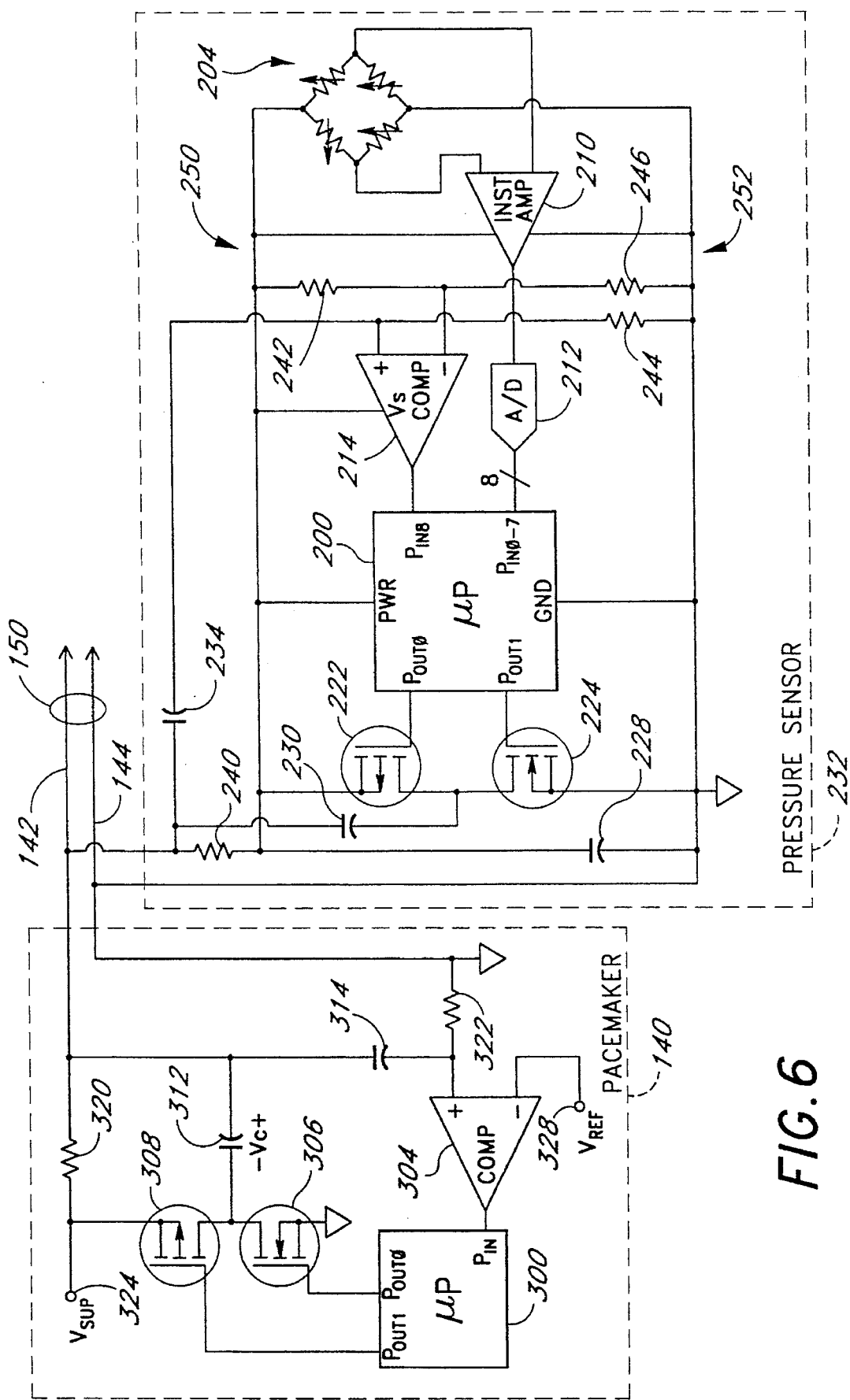
FIG. 6 is a circuit diagram for a pressure sensor, and for a pacemaker circuit that provides power to and communicates with multiple sensors over a two conductor bus.

FIG. 6 illustrates the circuitry of a pressure sensor 232 and a pacemaker 140 in accordance with a digital embodiment of the present invention. The pressure sensor 232 is connected to the pacemaker 140 by a two conductor bus 150 comprising bus lines 142 and 144. The pressure sensor 232 shown is capable conveying pressure data to the pacemaker 140, and is also capable of receiving control information from the pacemaker 140. Information transfer is accomplished under the control of software and using any of a variety of conventional modulation techniques. A pressure sensor of the type shown may be used, for example, to monitor pressure levels in the right ventricle during ventricular contractions.

The pressure sensor 232 comprises a microprocessor 200 (μP), a semiconductor bridge 204, an instrumentation amplifier 210, an analog-to-digital (A/D) converter 212, a comparator 214, switching transistors 222 and 224 (shown as P-channel and N-channel enhancement mode MOSFETs respectively, each having the source connected to the body), a local supply voltage/filtering capacitor 228, coupling capacitors 230 and 234, and resistors 240, 242, 244 and 246. The microprocessor 200 has an embedded read-only memory for storing program instructions (read-only memory not shown). The microprocessor 200 also has single-bit output ports $P_{OUT0}$ and $P_{OUT1}$, an 8-bit input port $P_{IN0-7}$, and a single-bit input port $P_{IN8}$. The semiconductor bridge 204 comprises four variable resistors that are mounted on a diaphragm (diaphragm not shown). The semiconductor bridge 204 is mounted such that the diaphragm flexes in response to increases in pressure, causing the variable resistors to vary in resistance in a controlled manner. The use of a semiconductor bridge for this purpose is known in the art.

The circuit components of the pressure sensor 232 are interconnected as follows. Two opposite terminals of the bridge 204 are connected to corresponding signal inputs of the instrumentation amplifier 210. The output of the instrumentation amplifier 210 is connected to the input of the analog-to-digital converter 212. The output of the analog-to-digital converter 212 is connected to the input port $P_{IN0-7}$. The output of the comparator 214 is connected to the input port $P_{IN8}$. The output ports $P_{OUT0}$ and $P_{OUT1}$ are connected to the respective gates of the transistors 222 and 224. The drains of the transistors 222 and 224 are connected to one another, and are connected to one terminal of the coupling capacitor 230. The other terminal of the coupling capacitor 230 is connected to the bus line 142. The coupling capacitor 234 is connected between the bus line 142 and the positive input of the comparator 214. One terminal of the local supply/filtering capacitor 228 is connected to local ground. The other terminal of the capacitor 228 is connected to each of the power input of the microprocessor 200, one terminal of the bridge 204, the power (PWR) input of the instrumentation amplifier 210, the supply voltage ($V_S$) input of the comparator 214, the source of the transistor 222, and one terminal of the resistor 242. The other terminal of the resistor 242 is connected to the negative input of the comparator 214. The resistor 244 is connected between the positive terminal of the comparator 214 and local ground. The resistor 246 is connected between the negative terminal of the comparator 214 and local ground. The source of the transistor 224 is connected to local ground.

The pacemaker 140 includes a microprocessor 300, a comparator 304, switching transistors 306 and 308 (shown as an N-channel enhancement mode MOSFET and a P-channel enhancement mode MOSFET respectively), coupling capacitors 312 and 314, a supply voltage source 324 that generates a DC voltage $V_{SUP}$ (typically 3 to 5 volts), and a reference voltage source 328 that generates a DC voltage $V_{REF}$ (typically 0.1 volts). The microprocessor 300 has an embedded read-only memory (not shown) for storing program instructions. The microprocessor 300 also has an input port $P_{IN}$ and two output ports $P_{OUT0}$ and $P_{OUT1}$. The input port $P_{IN}$ is connected to the output of the comparator 304. The output ports $P_{OUT0}$ and $P_{OUT1}$ are connected to the respective gates of the transistors 306 and 308. The source of the transistor 306 is connected to local ground. The source of the transistor 308 is connected to the supply voltage source 324. The drains of the transistors 306 and 308 are connected together. The coupling capacitor 312 is connected between the drains of the transistors 306 and 308 and the bus line 142. The coupling capacitor 314 is connected between the positive input of the comparator 304 and the bus line 142. The resistor 320 is connected between the supply voltage source 324 and the bus line 142. The resistor 322 is connected between the positive input of the comparator 304 and local ground. The negative input of the comparator 304 is connected to the reference voltage source 328.

The pressure sensor 232 and pacemaker 140 operate as follows. The supply voltage source 324 acts as a power source for the pressure sensor 232 and any other sensors on the bus 150. When no device is transmitting a signal on the bus 150, the voltage on the bus 150 is approximately equal to $V_{SUP}$. The supply voltage source 324 may be maintained in an off state to conserve battery power, and switched on only when a sample is to be taken from a sensor. When the supply voltage source 324 is switched on, the local supply/filtering capacitor 228 charges through the resistor 240. The charge stored by this capacitor 228 serves as a power source for the various active components of the pressure sensor 232, including the microprocessor 200, the instrumentation amplifier 210, the analog-to-digital converter 212 (power connection not shown), and the comparator 214. The capacitor 228 also provides power to the bridge 204. The resistor 240 in combination with the capacitor 228 serve as a filter for maintaining a generally constant local supply voltage level when one or more devices is transmitting on the bus 150. In an alternative embodiment of the pressure sensor 232, two additional switching transistors (not shown) are provided, each having its gate connected to an output port line of the microprocessor 200, to permit the microprocessor 200 turn off power to the bridge 204 and the instrumentation amplifier 210. The preferred locations of these additional switching transistors are shown generally by reference numbers 250 and 252.

An analog voltage which appears across the bridge 204 and the inputs of the instrumentation amplifier 210 represents the sensed pressure. This voltage is amplified by the instrumentation amplifier 210, and is digitized by the analog-to-digital converter 212. Samples of the digitized voltage are read by the microprocessor 200 via $P_{IN0-7}$, and transmitted to the pacemaker 140. The pressure sensor 232 may also transmit other types of information to the pacemaker 140. For example, the microprocessor 200 may be programmed to run a diagnostic test when power is initially applied to the bus 150, and to transmit the results of this test to the pacemaker 140.

The pacemaker 140 and pressure sensor 232 communicate by transmitting pulses on the bus 150 in accordance with a predetermined modulation technique. The microprocessor 300 of the pacemaker 140 transmits control information on bus 150 using the transistors 306 and 308 and the coupling capacitor 312, with the pair of transistors 306 and 308 acting as a three-state switch. The microprocessor 200 of the pressure sensor 232 similarly uses the transistors 222 and 224 and the coupling capacitor 230 to transmit data to the pacemaker 140. The control information transmitted by the microprocessor 300 of the pacemaker 140 may include sensor addresses for selecting one of multiple sensors on the bus 150. The control information may additionally include sensor commands. For example, for the alternative embodiment of the pressure sensor 232 described above, ON and OFF commands may be transmitted on the bus 150 to instruct the microprocessor 200 to turn on or off the power to the bridge 204 and the instrumentation amplifier 210.

The pacemaker 140 monitors pulses on the bus 150 via the coupling capacitor 314 and the comparator 304. Pulses detected by the comparator 304 are read into the microprocessor 300 via the input port $P_{IN}$. When the pacemaker 140 is in a transmit mode, the microprocessor 300 ignores pulses appearing at its input port. When the pacemaker 140 is in a receive mode, the transistors 306 and 308 are maintained in an off state so that no load is placed on the bus 150 by the pacemaker 140. The pressure sensor 232 receives pulses in an analogous manner, with the coupling capacitor 234 and comparator 214 used to detect pulses appearing on the bus 150, and with detected pulses being read into the microprocessor 200 via the input port $P_{IN8}$. The transistors 222 and 224 are maintained in an off state when the pressure sensor 232 is in a receive mode, so that no load is placed on the bus 150 by the pressure sensor 232.

It will be recognized from the foregoing that with the exception of the semiconductor bridge 204, all of the components of the pressure sensor 232 serve bus-related functions that are applicable to other types of sensors. These components can thus be replicated in other sensors that are connected to the bus 150. For example, a temperature sensor can be connected to the bus 150 that uses identical or similar bus circuitry to that of the pressure sensor 232, and which, in place of the semiconductor bridge 204, uses a voltage divider network with a thermistor. For purposes of the description that follows, it may be assumed that additional sensors similar to the pressure sensor 232 are connected to the bus 150.

In accordance with a preferred data transmission method, each sensor connected to the bus 150 transmits data on the bus 150 only when instructed to do so by the pacemaker 140. Thus, the sensors act as slaves with respect to the pacemaker 140, and the pacemaker 140 acts as a bus master. To instruct a sensor to transmit a data signal, the pacemaker 140 transmits an address (in the form of a series of pulses) that uniquely identifies a particular sensor. The pacemaker 140 may also transmit a command with the address. The addressed sensor then responds over a predetermined time interval by transmitting its physiologic data to the pacemaker 140. As will be recognized by those skilled in the art, various alternative methods exist for separating the data of the various sensors on the bus 150. For example, time division multiplexing could be used, with each sensor being assigned a unique time slot in which to transfer its data to the pacemaker 140, and with the pacemaker 140 controlling the timing of the time slots by periodically transmitting a synchronization signal. Alternatively, pulse frequency modulation could be used, with each sensor assigned a pulse frequency range within which to transfer its data. The specific transmission method used is implemented via the software that is executed by the microprocessor 300 of the pacemaker 140 and microprocessors of the various sensors.

The pacemaker 140 generates pulses on the bus 150 as follows. Initially, both transistors 306 and 308 are in a non-conductive or "off" state, and the voltage on the bus 150 is approximately $V_{SUP}$. To generate a single pulse, the microprocessor 300 initially turns on the transistor 306 (by outputting a logic high value on $P_{OUT0}$), allowing the capacitor 312 to charge through the resistor 320 to a voltage $V_C$. An associated drop in voltage on the bus 150 as the capacitor 312 charges is effectively ignored by the sensors. Once the capacitor 312 is sufficiently charged, the transistor 306 is turned off by the microprocessor 300 (by outputting a logic low value on $P_{OUT0}$), and the transistor 308 is immediately turned on (by outputting a logic low value on $P_{OUT1}$). When the transistor 308 is turned on, the voltage $V_C$ is added to the supply voltage $V_{SUP}$, producing a voltage of $V_{SUP}+V_C$ across the bus 150. The capacitor 312 discharges through the resistor 320 until the transistor 308 is turned off, at which time the bus voltage returns to $V_{SUP}$. A positive pulse (i.e., a temporary increase in voltage) is thus generated on the bus 150. This process is repeated each time the pacemaker 140 generates a pulse.

The pressure sensor 232 generates positive pulses on the bus 150 in a similar manner. To generate a pulse, the microprocessor 200 initially turns on the transistor 224 to charge the capacitor 230 from the bus 150. The microprocessor 200 then turns off the transistor 224 and turns on the transistor 222, to effectively switch the capacitor 230 in series with the capacitor 228. Since the capacitor 228 is initially charged to approximately $V_{SUP}$, a positive pulse is produced.

The pacemaker detects pulses appearing on the bus 150 as follows. When no devices are transmitting, the bus voltage 150 remains constant, and the coupling capacitor 314 filters out the DC voltage, producing a voltage of approximately zero volts at the positive input of the comparator 304. When a positive pulse appears on the bus 150, the voltage at the positive input of the comparator 304 increases above $V_{REF}$, causing the comparator 304 to switch from a logic-low to a logic-high value. The reference voltage $V_{REF}$ and coupling capacitor 314 are selected such that only positive pulses of a sufficient magnitude will cause the comparator 304 to switch. The change in voltage at the output of the comparator 304 is detected by the microprocessor 300 by monitoring $P_{IN}$, which may be configured to act as a positive-edge triggered interrupt input when the microprocessor 300 is in a receive mode. The pressure sensor 232 detects positive pulses is a similar manner via the coupling capacitor 234, comparator 214, and input port $P_{IN8}$. A positive reference voltage (typically 0.1 volts) is maintained at the negative input of the comparator 214 by the resistors 242 and 246, which act as a voltage divider network for dividing the voltage across the local supply/filtering capacitor 228.

While various embodiments of the present invention have been described, these embodiments have been presented by way of example only, and are not intended to limit the scope of the present invention. Thus, the breadth and scope of the present invention should be defined only in accordance with the following claims and their equivalents.

What is claimed is:

1. An apparatus for providing physiologic information to an implantable medical device, comprising:
   a pair of conductors adapted for connection to the medical device; and
   a plurality of implantable sensors, each sensor connected to said pair of conductors, each sensor having
   (a) a current receiving circuit for receiving a current from the medical device over said pair of conductors; and
   (b) a signalling circuit for generating and transferring an information signal to said medical device over said pair of conductors, wherein said signalling circuit generates said information signal by controlling a rate at which said current receiving circuit receives said current.

2. The apparatus according to claim 1, further comprising a pacing lead, wherein each of said plurality of sensors is positioned along said pacing lead and wherein said pair of conductors extends through at least a portion of said pacing lead.

3. The apparatus according to claim 1, wherein at least a portion of said current is used to supply power to circuitry of the respective sensor.

4. The apparatus according to claim 1, wherein said current receiving circuit comprises a capacitive element that charges in response to a voltage across said pair of conductors, said voltage supplied by the medical device.

5. The apparatus according to claim 1, wherein said current is received in pulses, and wherein said signalling circuit controls the timing of said pulses.

6. The apparatus according to claim 1, wherein said signalling circuit comprises a microprocessor.

7. The apparatus according to claim 1, wherein at least one of said sensors further comprises a bus monitoring circuit for receiving control signals from said medical device, said control signals provided by said medical device over said pair of conductors.

8. The apparatus according to claim 7, wherein said bus monitoring circuit comprises a microprocessor, said microprocessor programmed to respond to a predetermined address signal transmitted by said medical device.

9. An apparatus for adaptively pacing the heart, comprising:
   a pacemaker;
   a pacing lead adapted for connection to said pacemaker, said pacing lead having a pair of conductors that extend through at least a portion of said lead, said conductors connecting to said pacemaker when said pacing lead is connected to said pacemaker; and
   a plurality of physiologic sensors on said lead, each of said sensors connected to both of said conductors, wherein each sensor of said plurality comprises a charge storage circuit for receiving a current from said pacemaker over said pair of conductors and for storing a charge, said charge used to provide power to at least one active sensor component.

10. The apparatus according to claim 9, wherein said pacemaker comprises a voltage source for applying a supply voltage across said pair of conductors, said supply voltage supplying power to circuitry of said sensors.

11. The apparatus according to claim 10, wherein each sensor of said plurality comprises a signalling circuit for modulating said voltage across said pair of conductors to transfer an information signal to said pacemaker.

12. The apparatus according to claim 9, wherein at least one sensor of said plurality comprises a bus monitoring circuit for monitoring control signals provided on said pair of conductors by said pacemaker.

* * * * *